(12) United States Patent
Heismann et al.

(10) Patent No.: US 8,779,771 B2
(45) Date of Patent: Jul. 15, 2014

(54) MAGNETIC RESONANCE IMAGING SYSTEM AND METHOD EMBODYING A MAGNETIC RESONANCE MARKING SYSTEM AND METHOD

(75) Inventors: Bjoern Heismann, Erlangen (DE); Sebastian Schmidt, Weisendorf (DE); Markus Vester, Nuremberg (DE); Anke Weissenborn, Weil am Rhein (DE)

(73) Assignee: Siemens Aktiengesellschaft, Munich (DE)

( * ) Notice: Subject to any disclaimer, the term of this patent is extended or adjusted under 35 U.S.C. 154(b) by 411 days.

(21) Appl. No.: 13/213,253

(22) Filed: Aug. 19, 2011

(65) Prior Publication Data
US 2012/0043965 A1 Feb. 23, 2012

(30) Foreign Application Priority Data
Aug. 20, 2010 (DE) .......................... 10 2010 039 555

(51) Int. Cl.
*G01V 3/00* (2006.01)

(52) U.S. Cl.
USPC .......................................................... 324/314

(58) Field of Classification Search
USPC ........................... 324/300–322; 600/410–435
See application file for complete search history.

(56) References Cited

U.S. PATENT DOCUMENTS

| | | | |
|---|---|---|---|
| 6,682,492 B1 * | 1/2004 | Joensuu .......................... | 600/561 |
| 2003/0216636 A1 | 11/2003 | Paley et al. | |
| 2005/0054913 A1 * | 3/2005 | Duerk et al. ................... | 600/423 |
| 2005/0245811 A1 | 11/2005 | Scheffler | |
| 2007/0059247 A1 * | 3/2007 | Lindner et al. ............... | 424/9.52 |
| 2009/0174405 A1 | 7/2009 | Kassai | |
| 2010/0072985 A1 | 3/2010 | Kess | |

OTHER PUBLICATIONS

"Tailored RF Pulse for Magnetization Inversion at Ultrahigh Field," Hurley et al., Magnetic Resonance in Medicine, vol. 63 (2010) pp. 51-58.
"Arterial Spin-Labeling in Routine Clinical Practice, Part 1: Technique and Artifacts," Deibler et al., Am. J. Neuroradiology, vol. 29 (2008) pp. 1228-1234.

* cited by examiner

*Primary Examiner* — Dixomara Vargas
(74) *Attorney, Agent, or Firm* — Schiff Hardin LLP

(57) ABSTRACT

In a magnetic resonance marking system marking a flowing medium in a marking region, as well as in a magnetic resonance system with such a magnetic resonance marking system, a method to control a magnetic resonance marking system, and a method to generate magnetic resonance exposures, a radio-frequency transmission device generates marking radio-frequency signals, and a marking radio-frequency transmission coil emits the marking radio-frequency signals in the marking region. A magnetic field determination device determines a magnetic field strength in the marking region, and a control unit derives a marking transmission frequency from the determined magnetic field strength and to control the radio-frequency transmission device so that marking radio-frequency signals at the derived marking transmission frequency are emitted by the marking radio-frequency transmission coil.

12 Claims, 2 Drawing Sheets

MAGNETIC RESONANCE IMAGING SYSTEM AND METHOD EMBODYING A MAGNETIC RESONANCE MARKING SYSTEM AND METHOD

BACKGROUND OF THE INVENTION

1. Field of the Invention

The invention concerns a magnetic resonance marking system to mark a flowing medium in a marking region, of the type using a radio-frequency transmission device to generate marking radio-frequency signals and a marking radio-frequency transmission coil to emit the marking radio-frequency signals in the marking region. Moreover, the invention concerns a magnetic resonance system to generate magnetic resonance exposures of an examination region of an examination subject with such a magnetic resonance marking system. The invention also concerns a method to control a magnetic resonance marking system to mark a flowing medium in a marking region, in which method the marking radio-frequency signals are generated and emitted in the marking region. The invention also concerns a method to generate magnetic resonance exposures of an examination region of an examination subject in a magnetic resonance system in which a medium flowing into the examination region is marked beforehand in a marking region so that the medium is identified in magnetic resonance exposures of the examination region.

2. Description of the Prior Art

Magnetic resonance tomography has become a widespread technique to acquire images of the inside of the body of a living examination subject. In order to acquire an image with this method, i.e. to generate a magnetic resonance exposure of an examination subject, the body or the body part of the patient that is to be examined must initially be exposed to an optimally homogeneous static basic magnetic field (most often designated as a $B_0$ field), which is generated by a basic field magnet of a magnetic resonance system. Rapidly switched (activated) gradient fields for spatial coding that are generated by gradient coils are superimposed on this basic magnetic field during the acquisition of the magnetic resonance images. Moreover, RF signals (for example a radio-frequency pulse or a radio-frequency pulse sequence) of a defined field strength are radiated with a radio-frequency antenna into the examination volume in which the examination subject is located. The nuclear spins of the atoms in the examination subject are excited by means of this RF field (most often designated as a $B_1$ field) such that they are deflected out of their steady state, in which the spins are aligned parallel to the basic magnetic field, and precess around the direction of the basic magnetic field. For this purpose, the radio-frequency pulses must be radiated at the resonance frequency of the nuclear spins to be excited (known as the "Larmor frequency"), which depends on the magnetic field in which the atoms or molecules to be excited are located. The magnetic resonance signals that are thereby generated are received by radio-frequency reception antennas. The reception antennas can be either the same antennas with which the radio-frequency pulses are radiated, or separate reception antennas. The magnetic resonance images of the examination subject are reconstructed in a processor based on the received magnetic resonance signals. Each pixel in the magnetic resonance image is associated with a small physical volume (known as a "voxel") of the subject, and each brightness or intensity value of each pixel in the image is linked with the signal amplitude of the magnetic resonance signal that is received from the corresponding voxel.

A groundbreaking development in conventional magnetic resonance imaging has been techniques in which the perfusion of marked blood in the brain is acquired with the aid of a magnetic resonance apparatus. The blood supply in any region of the brain can be determined by a subtraction of two images: one with marked blood and one without marking. Brain activities can therefore be depicted, or variations of the blood flow can even be revealed in pathological cases such as strokes. The observation of the perfusion of blood or other marked bodily fluids can also be meaningful in other organs in order to more easily detect pathological cases.

Conventionally, the marking of blood has typically been implemented by the use of exogenic contrast agents based on gadolinium or the like. In order to be able to avoid the administration of such contrast agents, some time ago a technique known as the "ASL technique" (ASL=Arterial Spin Labeling) was developed, which is used particularly in the examination of the brain. The arterial blood in a marking region (for example in the neck region of the patient) is thereby electromagnetically marked (or "labeled") by special excitation of the nuclear spins in the blood (more specifically, the water component of blood) before it reaches an examination region (the brain, for example). An image is acquired after a certain period of time in which the blood marked in such a manner has become distributed in the brain.

As described above, a radio-frequency antenna is required for this purpose, with which the "normal" imaging radio-frequency signals required for the magnetic resonance acquisition are emitted into the examination region, for example the head region of the patient or test subject. The transmission antenna that serves to emit the imaging radio-frequency signals is also designated as an "imaging radio-frequency transmission antenna" or "imaging radio-frequency transmission coil" in the following. This imaging radio-frequency transmission antenna can be, for example, a "whole-body antenna" that is permanently installed in the magnetic resonance data acquisition unit that surrounds the examination space. However, it can also be a local antenna, for example a head coil that is placed on the patient like a helmet during the examination. In such examinations, it is thus possible to use the whole-body coil to emit the pulses and to use the head coil only to receive the magnetic resonance signals. In principle, however, the head coil can also be used to transmit the radio-frequency signals and to capture the magnetic resonance signals. In some magnetic resonance systems (for example Polestar by Odinmed, www.odinmed.com), basic field magnets and radio-frequency transmission antennas are fashioned and arranged so that they enclose only the head of the patient. A corresponding examination space or "field of view" of such a "head system" is thus markedly smaller than that of a "whole-body system".

To apply the ASL technique, an additional radio-frequency transmission antenna (designated in the following as a "marking radio-frequency transmission antenna" or "marking radio-frequency transmission coil") can be used that emits the aforementioned radio-frequency signals used for the marking. This marking antenna is typically directly arranged locally on the examination subject, advantageously as close as possible to a suitable artery of the patient. It is most often a relatively small radio-frequency transmission antenna.

The ASL technique functions very well in "whole-body" magnetic resonance systems in which both a marking region and an examination region are arranged in a magnetic field homogeneity volume. However, the ASL technique according to the prior art cannot be applied in magnetic resonance systems with a small homogeneity volume (for example in "head systems" of the aforementioned type). In such systems the homogeneity volume does not extend down to the carotid artery or the neck region of a patient, and thus the marking region lies outside of the magnetic field homogeneity region. Since the magnetic field strength outside the magnetic field homogeneity region declines quickly with increasing distance from the magnet or magnet system, the marking of the medium cannot take place with marking radio-frequency signals at the Larmor frequency that exists as a result of the basic magnetic field. Moreover, the imaging radio-frequency transmission antenna installed in the system cannot be used to mark the medium, because it does not extend into the neck region.

SUMMARY OF THE INVENTION

An object of the present invention is to provide an improved magnetic resonance marking system, a magnetic resonance system with such a magnetic resonance marking system, a method to control a magnetic resonance marking system, and a method to generate magnetic resonance exposures; that can be used universally, in particular in which the ASL technique can be applied even if the marking region is situated outside of the homogeneous volume of the basic magnetic field.

A magnetic resonance marking system in accordance with the invention has a magnetic field determination device to determine the magnetic field strength in the marking region as well as a control unit to derive a marking transmission frequency from the determined magnetic field strength. The control unit is additionally fashioned so that it activates the radio-frequency transmission device during operation so that marking radio-frequency signals of the derived marking transmission frequency are emitted via the marking radio-frequency transmission coil.

In a corresponding method to control a magnetic resonance marking system to mark a flowing medium in a marking region, marking radio-frequency signals are thus generated in a typical manner by means of a radio-frequency transmission device. These are emitted into the marking region via a marking radio-frequency transmission coil.

According to the invention the magnetic field strength in the marking region is initially determined to determine a suitable marking transmission frequency. The marking transmission frequency is subsequently derived based on the determined magnetic field strength. This is the Larmor frequency of the nuclei to be marked in the determined magnetic field, which Larmor frequency corresponds to the determined magnetic field strength.

The derivation of the frequency can be done, for example, by a calculation with a suitable formula that uniquely associates a frequency with a magnetic field strength for a defined particle type. A query to derive the sought frequency can likewise take place in a database in which the corresponding association data are stored. A frequency bandwidth can also be determined within which the frequencies of the marking radio-frequency signals should lie in order to thus also account for fluctuations of the magnetic field in the marking region.

The radio-frequency transmission device is then controlled so that marking radio-frequency signals of the derived marking transmission frequency are emitted.

One advantage of the magnetic resonance marking system according to the invention is that the marking radio-frequency transmission coil can be used in different magnetic resonance systems with different basic field magnets since the magnetic field strength is determined and the marking transmission frequency is adapted accordingly. The ASL technique is therefore also applicable in a simple manner to magnetic resonance systems that have only one magnet system with small magnetic field homogeneity volume (for example the aforementioned "head systems"), such that the marking region must lie outside of the magnetic field homogeneity volume. An additional advantage of the magnetic resonance marking system according to the invention is that the entire method can also be used specifically when the magnetic fields in the examination region and in the marking region are different. However, if the magnetic fields differ sufficiently in the regions, the Larmor frequencies also deviate so far from one another that an ASL excitation and an imaging measurement (i.e. an emission of imaging radio-frequency signals and/or a reception of magnetic resonance signals) can take place simultaneously without the marking system interfering with the imaging or vice versa.

A magnetic resonance system according to the invention for the generation of magnetic resonance exposures of an examination region of an examination subject can in principle be fashioned arbitrarily so that the marked medium flowing into the examination region is identifiable in magnetic resonance exposures of the examination region. However, it is essential that it be equipped with a magnetic resonance marking system according to the invention. Existing magnetic resonance systems can accordingly also be expanded (retrofitted) into a magnetic resonance system according to the invention by a simple refitting with a magnetic resonance marking system according to the invention.

In a method according to the invention to generate magnetic resonance exposures of an examination region of an examination subject in a magnetic resonance system, a medium flowing into the examination region is thus marked in a typical manner so that the medium is identified in the magnetic resonance exposures of the examination region. In accordance with the invention, the magnetic field strength is now determined in the marking region before marking, and based on this a suitable marking transmission frequency is determined for the emission of the marking radio-frequency signals.

There are various possibilities to determine the local magnetic field strength. It is taken into account that the magnetic field typically varies within the marking region, in particular when it is located at a boundary region of the magnetic field homogeneity volume, i.e. in a boundary region outside of the magnetic field homogeneity volume (for example immediately next to this). The determined magnetic field strength thus can simply be only an individual value of the magnetic field within the marking region, advantageously in a middle region of the marking region. However, multiple local individual values and/or an average of these values can likewise also be used to determine the marking transmission frequency. This is particularly useful in order to determine a frequency bandwidth for the frequencies of the marking radio-frequency signals.

Alternatively, a determination or calculation of the local magnetic field can be based on prior knowledge about the spatial magnetic field distribution in the boundary region of the magnetic field homogeneity volume of the magnet system that is used. For example, a magnetic field distribution map of a basic magnetic field can be generated and utilized for this purpose. For this, it is merely required that a position determination of the point at which the magnetic field should be determined—for example the location of the marking radio-frequency transmission coil—relative to the magnetic field system or in the coordinate system of the magnetic field distribution map.

For this purpose, the magnetic field determination device can have a position determination device and an interface (for example to a memory with a corresponding database) for the determination of information about the spatial magnetic field distribution. Moreover, such a database can also contain information as to how different patient types alter the magnetic field, i.e. information about the magnetic field distortion depending on physical properties. Alternatively, the database can already contain ready magnetic field distributions for various patient types (child, adult, male, female, different statures etc.). In principle the position determination device can have an interface for patient table control via which the table coordinates are accepted, which then determines the coordinates of the desired position (at which the magnetic field should be determined) relative to the magnet system on the basis of additional information about the position of the magnet and/or the attitude of the marking radio-frequency transmission coil and/or of the patient.

Alternative or additionally, the magnetic field strength can be measured locally at one or more points. This has the advantage that the magnetic field can be determined more precisely, at least locally, independent of a possible distortion of the field by the patient. A combination with a calculation with a previously known magnetic field distribution can thereby also take place, for example in that the measurement values are used in order to evaluate and, if necessary, adapt the distribution, and based on this to then determine local magnetic field values more precisely at locations other than the measurement locations.

The magnetic field determination device can have a magnetic field measurement device, for example a Hall probe, to measure the magnetic field strength.

Such a magnetic field measurement device, in particular a Hall probe, can be directly installed in the marking radio-frequency transmission coil.

A Hall probe can measure the magnetic field strength only in one spatial direction. A complete 3D vector of the magnetic field in space can be determined locally by a preferred combination of three magnetic field sensors (in particular Hall probes) aligned orthogonally to one another.

For a more precise measurement of the magnetic field strength in the marking region, multiple magnetic field sensors arranged adjacently can be used in the magnetic field measurement device. A gradient of the magnetic field in the corresponding region can also be determined by, for example, the measurement values of the two magnetic field sensors being separated by the spatial distance of the magnetic field sensors. The knowledge of one or more local gradients enables the magnetic field to be better estimated in the entire marking region, and thus also allows a marking transmission frequency bandwidth to be better adapted to the extent of the marking region.

As explained above, the magnetic resonance system typically has a basic field magnet with a defined magnetic field homogeneity volume. The basic field magnet or its magnetic field homogeneity volume is fashioned and arranged so that the examination region lies within the magnetic field homogeneity volume. As explained in principle, the invention allows that the marking radio-frequency transmission coil to also be fashioned and arranged so that the marking region is situated in a boundary region of the magnetic field homogeneity volume. Nevertheless, the invention can also be used when the marking region also lies within the magnetic field homogeneity volume. In this case the magnetic resonance marking system can, for example, be fashioned as an autarchic system that does not require any data of the magnetic resonance system regarding the current magnetic field or the marking transmission frequency to be emitted.

If the magnetic field strength in the examination region and the magnetic field strength in the marking region have a sufficiently large difference, this enables magnetic resonance exposures to be generated with an ASL technique in which the marking transmission frequency and the imaging transmission frequency are selected so that a marking transmission frequency bandwidth and an imaging transmission frequency bandwidth do not significantly overlap. This means that the center frequency and the bandwidth of the marking transmission frequency as well as the center frequency and the bandwidth of the imaging transmission frequency are situated so that they do not significantly overlap, such that at the same time the marking and the magnetic resonance imaging can take place at two different frequencies without these two procedures mutually interfering. Such a method can also be used independently of whether the magnetic resonance marking system has a magnetic field determination device, insofar as it is ensured that the magnetic field strengths in the examination region and in the marking region differ sufficiently and a matching marking transmission frequency is communicated to the control unit of the magnetic resonance marking system independent of the imaging transmission frequency.

If the marking and the magnetic resonance exposures take place simultaneously at different frequencies, in order to avoid any influence of the marking radio-frequency signals on the reconstructed images, filters can additionally be used in the reception unit to avoid an overdriving of the receiver and/or noise injection by the marking radio-frequency transmission coil.

DESCRIPTION OF THE PREFERRED
EMBODIMENTS

Figure 1:
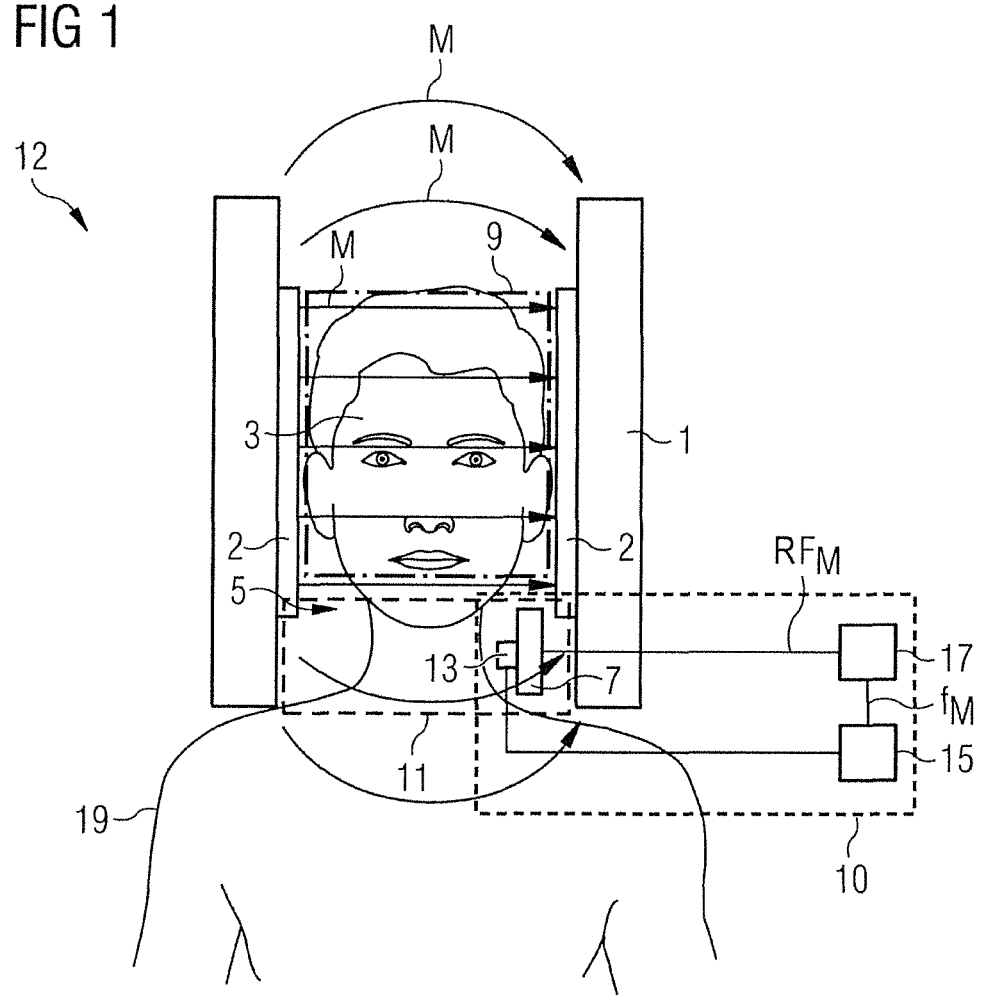
FIG. 1 is a schematic representation of an exemplary embodiment of a magnetic resonance system according to the invention, with a first exemplary embodiment of a magnetic resonance marking system according to the invention.

FIG. 1 shows a design of a magnetic resonance system according to the invention in the form of a "head system". A basic field magnet 1 generates an optimally homogeneous basic magnetic field (symbolized by the magnetic field lines M) within a magnetic field homogeneity volume 3. An examination region—here the head region of a patient 19—is located in this homogeneity volume 3. Known gradient coils (not shown) generate rapidly switched gradient fields for spatial coding. These gradient fields overlap the basic magnetic field. Moreover, imaging magnetic resonance signals to excite the nuclear spins in the examination region 9 are emitted by means of an imaging radio-frequency transmission antenna 2. Magnetic resonance signals that are thereby induced are acquired by a radio-frequency reception antenna, wherein the imaging radio-frequency transmission antenna 2 is also used for this. The acquired magnetic resonance signals are amplified in a typical manner, passed to a reception system and additionally processed there. The magnetic resonance images of the examination subject are then reconstructed on the basis of the received magnetic resonance signals. The principle design and the mode of operation of such a magnetic resonance system are known to those skilled in the art and need not be explained in more detail herein.

The magnetic resonance system 12 is equipped with a magnetic resonance marking system 10 according to the invention. The magnetic resonance marking system 10 has a marking radio-frequency transmission coil 7, a radio-frequency transmission device 17, a control unit 15 and a magnetic field determination device 13, here in the form of an individual Hall probe system 13 formed by three Hall probes arranged orthogonally to one another.

The marking radio-frequency transmission coil 7 is fed by the radio-frequency transmission device 17 with marking radio-frequency signals $RF_M$ with a specific marking transmission frequency $f_M$ that are then emitted into a marking region 11 (here a slice through the next region of the patient 19 that is situated perpendicularly to the longitudinal axis of the patient) in order to mark the blood flowing through the arteries there into the head. For this the marking radio-frequency transmission coil 7, which here is designed as a typical carotid reception coil, is attached at the neck of the patient 19. Alternatively, a coil of a different design, for example a circularly polarized coil (for example a type of birdcage coil), can also be used as a marking radio-frequency transmission coil. The marking radio-frequency transmission coil can particularly preferably also comprise multiple coil elements with different resonance frequencies from which the suitable coil element is selected depending on the determined marking transmission frequency.

The marking region 11 in the shown magnetic resonance system 12 is located in a boundary region outside of the magnetic field homogeneity volume 3.

The Hall probe is arranged in the marking region 11; in the preferred variant shown here it is arranged directly in a housing of the marking radio-frequency transmission coil 7. This Hall probe 13 measures the magnetic field strength in the marking region 11 and passes the measured value to the control unit 15, which is connected with the magnetic field determination device 13.

The control unit 15 derives a matching marking transmission frequency $f_M$ (the Larmor frequency corresponding to the measured magnetic field strength) from the determined magnetic field strength and activates the radio-frequency transmission device 17 so that marking radio-frequency signals $RF_M$ are emitted by the marking radio-frequency transmission coil 7 at the determined marking transmission frequency $f_M$ or, respectively, in a defined frequency range around this frequency. The frequency range can be selected by the control unit to match the variation width of the magnetic field strength within the total marking region 11. The marking radio-frequency transmission coil 7 is fashioned so that it can emit marking radio-frequency signals in the frequency range.

Figure 2:
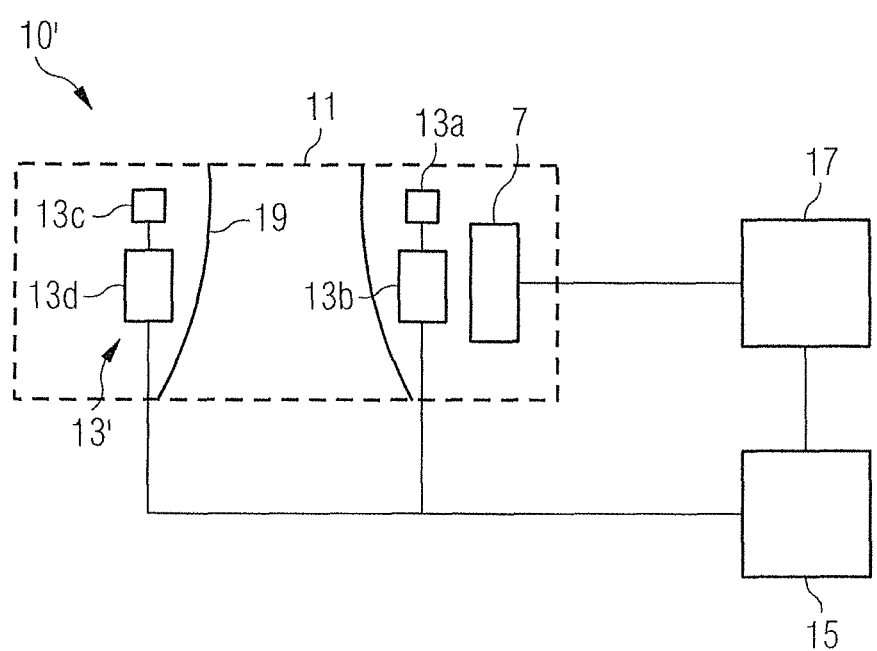
FIG. 2 is a schematic representation of an alternative exemplary embodiment of a magnetic resonance marking system according to the invention.

FIG. 2 is a schematic presentation of an alternative exemplary embodiment of a magnetic resonance marking system according to the invention. In this variant the magnetic field determination device 13 respectively has two Hall probe systems 13a, 13b, 13c, 13d (comprising three respective, orthogonal Hall probes) on both sides of the neck of the patient 19.

The magnetic field strength can be measured at multiple points by means of multiple Hall probes 13a, 13b, 13c, 13d. From this the gradient of the magnetic field can be at least locally determined, and thus a bandwidth of the marking transmission frequency (the bandwidth corresponding to the thickness of the marking region) can be determined more simply. In the example shown in FIG. 2, local gradients to the right and left of the neck in the longitudinal direction of the patient and at the head end and the middle of the marking slice transversal to the neck can respectively be determined from the magnetic field strengths measured by the Hall probe systems 13a, 13b, 13c, 13d and the geometric intervals between said Hall probe systems 13a, 13b, 13c, 13d.

The determination of the magnetic field strength and the adaptation of the marking transmission frequency can take place in real time so that possible changes of the magnetic field strength (due to gradient action, for example) directly affect the marking transmission frequency.

The emission of the marking radio-frequency signals in the marking region can also take place given deactivated gradient coils since a "natural" gradient exists outside of the magnetic field homogeneous volume 3 due to the inhomogeneity of the field.

An advantage of the magnetic resonance marking system according to the invention is that the marking radio-frequency transmission coil 7 can be used in different magnetic resonance systems with different basic magnetic field strengths since the magnetic field strength is determined and the marking transmission frequency is adapted accordingly. The invention also allows the ASL technique to be used when the marking region lies outside of the homogeneity volume of the basic magnetic field, for example given magnetic resonance systems with small "field of view".

The invention is not limited to use in magnetic resonance systems with the geometries shown in FIG. 1, but also can be used in any magnetic resonance apparatuses, in particular in systems with very small, short solenoid magnets.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance marking system for marking a flowing medium in a marking region, comprising:
   a radio-frequency device that generates marking radio-frequency electrical signals;
   a marking radio-frequency transmission coil, supplied with said marking radio-frequency electrical signals, that radiates a marking radio-frequency field in the marking region corresponding to the marking radio-frequency electrical signals, the marking radio-frequency field interacting with nuclear spins of the flowing medium to mark the nuclear spins of the flowing medium by arterial spin labeling;
   a magnetic field determination device that determines a magnetic field strength that exists in said marking region during said radiation of said radio-frequency field; and
   a control unit configured to derive a marking transmission frequency from a known relation thereof to the magnetic fields strength determined by said magnetic field determination device, and to control the radio-frequency device to generate said marking radio-frequency electrical signals so as to cause the marking radio-frequency field, emitted by the marking radio-frequency transmission coil to be radiated at the derived marking transmission frequency.

2. A magnetic resonance marking system as claimed in claim 1 wherein said magnetic field determination device comprises a magnetic field measurement device.

3. A magnetic resonance system as claimed in claim 2 wherein said magnetic field measurement device comprises a set of three magnetic field sensors respectively aligned or orthogonally to one another.

4. A magnetic resonance marking system as claimed in claim 2 wherein said magnetic field measurement device comprises multiple magnetic field sensors located adjacent to each other, to collectively determine a magnetic field gradient.

5. A magnetic resonance marking system as claimed in claim 2 wherein said marking radio-frequency transmission coil has a housing, and wherein said magnetic field measurement device is located on or in said housing.

6. A magnetic resonance marking system as claimed in claim 1 wherein said magnetic field determination device comprises a position determination device and an interface that determines information describing a spatial magnetic field distribution of said magnetic field strength.

7. A magnetic resonance system comprising:
a magnetic resonance data acquisition unit comprising a basic field magnet that generates a basic magnetic field having a magnetic field strength;
a radio-frequency device that generates marking radio-frequency electrical signals;
a marking radio-frequency transmission coil, supplied with said marking radio-frequency electrical signals, that radiates a marking radio-frequency field in the marking region corresponding to the marking radio-frequency electrical signals, the marking radio-frequency field interacting with nuclear spins of the flowing medium to mark the flowing medium by arterial spin labeling;
a magnetic field determination device that determines the magnetic field strength that exists in said marking region during said radiation of said radio-frequency field; and
a control unit configured to derive a marking transmission frequency from a known relation thereof to the magnetic fields strength determined by said magnetic field determination device, and to control the radio-frequency device to generate said marking radio-frequency electrical signals so as to cause the marking radio-frequency field, emitted by the marking radio-frequency transmission coil to be radiated at the derived marking transmission frequency.

8. A magnetic resonance system as claimed in claim 7 wherein said basic field magnet generates said basic magnetic field with a magnetic field homogeneous volume in which said examination region is located, and wherein said marking radio-frequency transmission coil is located and configured to cause said marketing region to be located in a boundary region of said magnetic field homogeneous volume.

9. A method to control a magnetic resonance marking system for marking a flowing medium in a marking region, comprising:
with a radio-frequency transmission device, generating electrical radio-frequency marking signals;
from a marking radio-frequency transmission coil, supplied with said marking radio-frequency electrical signals, radiating a radio-frequency marking field corresponding to the marking radio-frequency electrical signals into a marking region in which said flowing medium is located, said marking radio-frequency field interacting with nuclear spins of said flowing medium in said marking region to mark the nuclear spins of the flowing medium by arterial spin labeling;
with a magnetic field determination device, determining a magnetic field strength that exists in said marking region during said radiation of said radio-frequency field;
in a computer, deriving a marking transmission frequency from a known relation thereof to the determined magnetic field strength; and
from the computer emitting a control signal to automatically said radio-frequency device that operate said radio-frequency device to generate said marking radio-frequency electrical signals so as to cause said radio-frequency marking field to be radiated at the derived marking transmission frequency.

10. A method to generate a magnetic resonance exposure of an examination subject having a flowing medium therein, comprising the steps of:
with a radio-frequency transmission device, generating electrical radio-frequency marking signals;
from a marking radio-frequency transmission coil, supplied with said marking radio-frequency electrical signals, radiating a radio-frequency marking field corresponding to the marking radio-frequency electrical signals into a marking region in which said flowing medium is located, said marking radio-frequency field interacting with nuclear spins of said flowing medium in said marking region to mark the nuclear spins of the flowing medium by arterial spin labeling;
with a magnetic field determination device, determining a magnetic field strength that exists in said marking region during said radiation of said radio-frequency field;
in a computer arrangement, deriving a marking transmission frequency from a known relation thereof to the determined magnetic field strength; and
from the computer emitting a control signal to automatically said radio-frequency device that operate said radio-frequency device to generate said marking radio-frequency electrical signals so as to cause said radio-frequency marking field to be radiated at the derived marking transmission frequency; and
in said computer arrangement, acquiring magnetic resonance data from the subject in said examination region, after marking said nuclear spins of said flowing medium, and reconstructing a magnetic resonance image of the subject, that includes the flowing medium, from said magnetic resonance data, and making said magnetic resonance image available in electronic form at an output of said computer arrangement.

11. A method as claimed in claim 10 comprising acquiring said magnetic resonance data with a magnetic resonance data acquisition device and, in said magnetic resonance data acquisition device, generating a basic magnetic field having a magnetic field homogeneous volume in which said marking radio-frequency transmission coil is located to cause said marking region to be located at a boundary region of said magnetic field homogeneous volume.

12. A method to control a magnetic resonance marking system for marking a flowing medium in a marking region, comprising:
with a radio-frequency transmission device, generating electrical radio-frequency marking signals;
from a marking radio-frequency transmission coil, supplied with said marking radio-frequency electrical signals, radiating a radio-frequency marking field corresponding to the marking radio-frequency electrical signals into a marking region in which said flowing medium is located, said marking radio-frequency field interacting with nuclear spins of said flowing medium in said marking region to mark the nuclear spins of the flowing medium by arterial spin labeling;
with a magnetic field determination device, determining a magnetic field strength that exists in said marking region during said radiation of said radio-frequency field;

in a computer arrangement, deriving a marking transmission frequency from a known relation thereof to the determined magnetic field strength; and from the computer emitting a control signal to automatically said radio-frequency device that operate said radio-frequency device to generate said marking radio-frequency electrical signals so as to cause said radio-frequency marking field to be radiated at the derived marking transmission frequency;

from said computer arrangement, controlling acquisition of magnetic resonance data from the subject, including radiating an imaging radio-frequency field, at an imaging transmission frequency, into the subject simultaneously with said radiating of the radio-frequency marking field; and in said computer arrangement, selecting a marking transmission frequency bandwidth for said marking transmission frequency, and an imaging transmission frequency bandwidth for said imaging transmission frequency, that have substantially no overlap with each other.

* * * * *